(12) United States Patent
Lieberman et al.

(10) Patent No.: US 8,475,172 B2
(45) Date of Patent: Jul. 2, 2013

(54) MOTOR LEARNING AND REHABILITATION USING TACTILE FEEDBACK

(75) Inventors: Jeff Lieberman, Cambridge, MA (US); Cynthia Breazeal, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1345 days.

(21) Appl. No.: 11/780,348

(22) Filed: Jul. 19, 2007

(65) Prior Publication Data

US 2009/0023122 A1    Jan. 22, 2009

(51) Int. Cl.
*A63B 69/00* (2006.01)
*A61N 1/00* (2006.01)

(52) U.S. Cl.
USPC ............................. 434/258; 434/247; 607/49

(58) Field of Classification Search
USPC ........................ 434/247, 257, 258; 607/48, 49
See application file for complete search history.

(56) References Cited

U.S. PATENT DOCUMENTS

| | | | | |
|---|---|---|---|---|
| 5,554,033 | A * | 9/1996 | Bizzi et al. | 434/247 |
| 5,679,004 | A * | 10/1997 | McGowan et al. | 434/247 |
| 5,697,791 | A * | 12/1997 | Nashner et al. | 434/247 |
| 5,794,621 | A * | 8/1998 | Hogan et al. | 600/407 |
| 6,028,593 | A * | 2/2000 | Rosenberg et al. | 345/156 |
| 6,059,576 | A * | 5/2000 | Brann | 434/247 |
| 6,774,885 | B1 * | 8/2004 | Even-Zohar | 345/156 |
| 6,778,866 | B1 * | 8/2004 | Bettwy | 700/56 |
| 7,033,281 | B2 * | 4/2006 | Carnahan et al. | 473/221 |
| 7,098,776 | B2 | 8/2006 | Chang et al. | |
| 7,305,268 | B2 * | 12/2007 | Gliner et al. | 607/45 |
| 7,349,739 | B2 * | 3/2008 | Harry et al. | 607/49 |
| 2003/0170602 | A1 * | 9/2003 | Hagita et al. | 434/307 R |
| 2004/0219498 | A1 * | 11/2004 | Davidson | 434/247 |
| 2005/0187071 | A1 * | 8/2005 | Yamashita et al. | 482/1 |
| 2007/0146371 | A1 * | 6/2007 | Dariush | 345/474 |

OTHER PUBLICATIONS

Holden, Maureen K., "Virtual Environments for Motor Rehabilitation: Review," CyberPsychology & Behavior, 2005;8(3):187-211.
Jones, Lynette A., et al., "Development of a Tactile Vest," HAPTICS '04, IEEE 0-7695-2112-6/04, 8pp.
Lieberman, Jeff, "Accelerated and Improved Motor Learning and Rehabilitation using Kinesthetic Feedback," Thesis, MIT, Aug. 2006, 71pp.
Rose, F.D., et al., "Training in virtual environments: transfer to real world tasks and equivalence to real task training," Ergonomics, Apr. 2000;43(4):494-511, Abstract.
Rupert, A.H., "An instrumentation solution for reducing spatial disorientation mishaps," Engineering in Medicine & Biology Magazine, IEEE, Mar./Apr. 2000;19(2):71-80, Abstract.
Summers, Ian R., Ed., "Tactile Aids for the Hearing Impaired, Temporal Domain," 1992, 33pp.

(Continued)

*Primary Examiner* — Kang Hu
(74) *Attorney, Agent, or Firm* — SoCal IP Law Group LLP; John E. Gunther; Steven C. Sereboff (57) ABSTRACT

There is disclosed a process for motor learning, for teaching motion, or for rehabilitation of a student, the student having a motor sensory system. Plural transducers may be coupled around at least one joint of a student, the transducers for providing kinesthetic sensations to the student through its motor sensory system. Tactile control signals may be provided to control operation of the transducers to guide motions of the student.

18 Claims, 6 Drawing Sheets

OTHER PUBLICATIONS

Todorov, Emanuel, et al., "Augmented Feedback Presented in a Virtual Environment Accelerates Learning of a Difficult Motor Task," Journal of Motor Behavior Jun. 1997;29(2):147-158.

Wall, Conrad, III, et al., "Balance Prostheses for Postural Control," IEEE Engineering in Medicine and Biology Magazine, Mar./Apr. 2003, 0739-5175/03:84-90.

* cited by examiner

MOTOR LEARNING AND REHABILITATION USING TACTILE FEEDBACK

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

BACKGROUND

1. Field

This disclosure relates to motor learning and rehabilitation using kinesthetic feedback.

2. Description of the Related Art

Roughly 8% of Americans have some motor skill inability. Victims of neurological trauma such as stroke form an especially interesting segment of the disabled population, because after stroke, the victims still possess adequate muscle mass, but no way to control it. The longer muscle retraining requires, the more injury can result to the body through accidents or body misuse.

On the other end of the spectrum, sports players and artists such as dancers depend on accurate motion to perform. Those that have the greatest control over their motor system perform best, and learning this control can take many years.

Typically both of these segments of the population improve their skills with a teacher—a professional who helps them improve their motor system skills. The novice/patient has three primary communication channels by which to learn new skills: auditory, usually providing high level information, or current state of performance; visual, by watching the teacher, and themselves as they attempt to perform; and tactile, through both the touch of a teacher in helping along certain motions, and in kinesthetic knowledge about one's own position/movement. A teacher cannot, however, provide real-time feedback for a novice in an efficient manner—humans have too many joints functioning in parallel, a teacher gets 'in the way' while touching a student, and a teacher uses subjective evaluation of performance, some aspects of which can be better examined by a computer vision system for accuracy. Motor learning has been a subject of active research for over fifty years, and yet no deep understanding of mechanisms and methods has been found. Historically the study of motor skills learning came after World War II, when devices were developed to help Air Force pilots gain more information while flying, without requiring visual attention such as tilt readings. As early as the late forties it was known that feedback played an important role in motor learning. Below details describe the nature of motor feedback, and its importance in learning.

One point of note in agreement in the study of motor skill development is that feedback is crucial to levels of performance. Feedback provides three necessary components in learning: reward, information, and motivation. Even the knowledge of the sign of the errors in a ranging task was shown to improve a gunnery trainer's performance.

The time at which feedback is given is also extremely influential in human performance. Timely or near real-time feedback greatly enhances behavior and motor skill learning. It has been found that a student's ability to use feedback is seriously disrupted or made impossible if the feedback lags performance by 1.0 seconds or more.

The primary touch organ, skin, is the largest organ of the human body. The skin is very sensitive to periodic applied pressure, or vibration. Within this document, the application of period pressure to the skin will be referred to as vibrotactile stimulation. The sensitivity of the skin varies with the frequency of the applied pressure. Skin experiences its highest response to inputs of 250 Hz, and falls off at higher frequencies. Furthermore, our frequency sensitivity is sensitive to contactor size (the size of the element contacting the skin). Smaller contactors possess a flatter curve of sensitivity across frequencies, indicating that when small contactors are used the threshold response is independent of frequency. At higher frequencies (e.g., 80-230 Hz), sensitivity increases directly with contactor size.

We respond to frequencies differently in different ranges, especially differentiating between below and above 100 Hz. Furthermore, frequency content (harmonics) plays a role in tactile identification. Our ability to discriminate between frequencies is reasonable at lower frequencies but deteriorates rapidly as frequency is increased. The skin is rather poor at frequency discrimination. Pulses produce better discrimination than do sine waves.

The skin's ability to detect short signals depends on contactor size. The ability to detect gaps on skin impulses exists until roughly 10 ms, but is as low as 5 ms for highly damped mechanical pulses. Bursts of sinusoids are significantly easier to detect than bursts of noise. Sinusoids are felt as 'smooth' and the gap is perceived as a small click, whereas noise feels 'rough' and the gap is perceived as a modulus of stimulus amplitude.

When stimulus elements for sequences is increased to five or six, stimulus onset intervals needed for correct identification of the temporal sequence may be nearly 500 ms. This results in a 'too slow' perception for real time speech, for example. However, to simply discriminate between two temporal sequences with no requirement to identify temporal order, increasing the number of stimulus elements has little effect on performance and discrimination thresholds are generally below 100 ms.

One amazing aspect possessed by our somatosensory system is known as sensory saltation. It is best described with an example: We place three tactile transducers on the skin, one at the wrist, one ten cm up the arm, and one ten cm further. We apply five brief pulses to the wrist, then without any break in the regularity of the pulses, five more on the second transducer, and then five at the final transducer. The taps will seem to be distributed, contrary to our default bias, and seem to be spaced uniformly, more or less, from the region of the first contactor to that of the third.

Several conditions are necessarily met to create this saltatory illusion. Although even two pulses per location is adequate, the effect is most pronounced with four-six pulses per location. Any irregularity of the pulse sequence timing disturbs what has become called the 'cutaneous rabbit.' Contactors can be placed as close as 2 cm apart, and as far as 35 cm apart, while still causing the hopping effect.

Although regularity in timing is very important, the timing between taps is not highly critical. A pronounced effect occurs over a wide range of interstimulus interval values (ISIs). We begin to notice the effect with an ISI of 200 msec, and it settles into an evenness at 100 msec. Upon reaching 50 msec ISI, the hopping effect is optimal in regularity and vividness. It has been found that with further shortening of the ISI, the perceived number of taps becomes illusory.

The saltation effect works equally well with electro-tactile stimulation as with vibrotactile pulses. When receiving these signals, often there is the impression that the taps extend beyond the terminal contactor. This effect is related to 'synthetic movement' and the 'phi phenomenon' present in the visual sensory system.

A great deal of work has been done in the last decade studying the benefits of augmented feedback, primarily given visually through a Virtual Reality (VR) environment. A key factor of motor learning is that motor repetition is not enough to "induce cortical correlates of motor learning." The practice done by the subject must be linked to incremental success at some task or goal. Trial and error practice with feedback about performance success accomplishes this, with feedback gained through the senses.

Augmented feedback can enhance the cortical changes associated with motor learning. Virtual reality is one methodology by which we can add augmented feedback, but none of the gains have been shown to be peculiar to VR. With augmented feedback, we receive both proprioceptive (one's sense of body position) and exteroceptive (one's sense of stimuli outside of the body) feedback associated with the execution of a task, which induces profound cortical and subcortical changes at the cellular and synaptic level. Visual recognition of a teacher performing a task correctly stimulates mirror neurons for learning.

Typically, the augmented feedback given is a visual display of the subject's motion, as well as a visual display of the 'correct' motion, as performed by a coach or teacher. Both motions are tracked in real-time so the user at all times can see how their motion differs from the desired motion. In stroke motor rehabilitation experiments, not only did motions learned in VR translate into the real world, but they also generalized to motor learning in untrained spatial locations.

Learning to perform a task consists of two primary parts:
Finding the set of constraints that any movement must satisfy for success
Selecting a subset of movements easiest to produce and control to perform reliably
These movements are known as task related invariants.

One possible way to teach task constraints is to provide reference movements that satisfy the constraints. Therefore, one role of augmented feedback, it has been suggested, might be to emphasize the differences between the subject's movements and the reference movement. There is psychophysical evidence that humans derive specifications of movement by tracking end-effector trajectories (of the limb, usually). By explicitly showing this trajectory through a VR display, learning may be enhanced, especially in the initial phase.

Tactors (tactile actuators) are transducers that were originally developed for sensory substitution, primarily for the deaf-blind community. By applying force to the skin, we can transmit coded information. The initial projects that accomplished this were such as the Teletactor (developed in 1931 by Robert Harvey Gault), an array of 32 actuators presenting sound, the Optacon (developed in the 1960s by Dr. James Bliss), a 6×24 array of actuators responding to light input (to translate written text into tactile stimulation), and the Videotact (produced in 1996 by the Unitech Company), which possess 768 electro-tactile actuators to present video. These devices 'substituted' a tactile channel for the more typical auditory and visual channels one would use to process such information.

The historical development of tactile interfaces always focused on this channel substitution, relegating visual or auditory information to the somatosensory channel.

DETAILED DESCRIPTION

Throughout this description, the embodiments and examples shown should be considered as exemplars, rather than limitations on the apparatus and methods disclosed or claimed.

An augmented sensory feedback system is described. One apparatus is a lightweight comfortable wearable tactile feedback device that utilizes the communication channel of direct touch on the body, to give real-time feedback to the wearer about their performance in motor skill tasks. Using tactile signals to indicate joint error in a user's motion, we enable a user to wear a full-body suit that provides subtle cues for the brain, as they perform a variety of motor skill tasks. Tactile real-time feedback may act as a dance teacher or physical therapist does: by giving muscle aid through informational touch cues, not only through force or torque. This may enable people to undergo constant therapy/training, over all joints of the body simultaneously, with higher accuracy than a therapist/teacher provides.

Though described with respect to human users, the processes and apparatus described herein may be used with other animals (i.e., a mammal, a bird, a fish, a reptile or an amphibian). The processes and apparatus could be used with nearly any animal having a motor sensory system.

The person or animal wearing the tactile feedback suit is referred to as a student, though the person may be a novice, a patient, or some other person who will be engaged in motor learning or rehabilitation. Likewise, a teacher may be the source of the motor information, and the teacher may be, for example, an artist, an expert or a therapist.

The tactile feedback suit may enable more rapid motor rehabilitation and postural retraining to combat repetitive strain injuries (RSIs). It may also allow communication between a motion expert and a student in real-time (e.g., by comparing the student's performance to an expert's), to aid in higher level motor learning skills for activities such as sports and dance. The tactile feedback suit may be used to train students for sports such as golf, tennis, and martial arts. The tactile feedback suit may also be used to train students for ballet and other forms of dance and for musical activities such as playing the guitar, piano or other instrument. The tactile feedback suit may also be used to train students in the operation of vehicles and other equipment such as military, excavation or construction equipment. It may function as a tool to accelerate and deepen peoples' motor learning capabilities.

This description focuses on transducer selection and feedback mechanisms for such a suit, in a low-joint-number test, comprising elements of the upper arm. It should be understood that the upper arm is an example, and the apparatus and methods described herein can be applied to any other joint or combinations of joints, up to and including a full body tactile feedback suit for training full body movements.

Practicing incorrect motions during motor training can actually deteriorate users' skills, and may cause injury during the training process, as well as slow down the overall learning curve. It is very important in expert training of novices, that correct and precise motions be made properly as early as possible, before the student begins motor-learning improper motions. Feedback about performance is believed to be the single most important element of learning motor skills. However, even an expert is unable to observe a student's behavior omnipotently. Furthermore, when the teacher leaves the student, performance often fades and bad habits and behaviors often supersede skills learned moments earlier. Constant real-time monitoring and feedback of an expert, as well as the ability to monitor many facets of a user's performance synchronously, may minimize the time it takes to learn a new motor-skill—quickened feedback enhances learning. Indeed, performance may be seriously disrupted or made impossible by lags of feedback of even less than 1.0 sec. We have a great ability to improve upon the typical 'this is what you did wrong' teaching method, which relies on more distant performance. Even knowing only the sign of an error in motion has been useful in accelerating motor training.

Teachers cannot be infallible when observing students, but they can be closer when performing the behaviors themselves. This is because they do many things of which they are no longer even conscious, through their use of motor memory. A teacher can quite often perform a very difficult task, without being able to explain in words how it is done. Spoken language is an indirect method of communicating movement—movement itself, proprioception, and touch are more direct. Typically, the most useful task a teacher can do is correct the student as they perform the desired task, by moving the student's muscles in the right way, with direct tactile feedback—this is especially true in dance and the sports arenas (e.g., golf swings). Often times it is not enough for the novice to observe the expert visually and through language, as they miss subtle cues that make certain movement possible, and because direct muscle stimulation is a more direct path to motor learning than through language describing motor skills.

The goal of this system is to become a real-time, full-time, highly parallel motor skills teacher, by giving constant direct motor-system feedback to the user, as novices attempt new tasks, or patients attempt to re-attain motor skills.

A suit worn by both an expert and an novice, as well as a software control system and motion control capture device are now described. Its behavior is guided by motor learning principles. The system enables full body tracking of all joints, in real-time. These may be recorded and stored while the expert performs the desired task (e.g., a dance maneuver), on a 3D model of the expert.

The examples used in this description and the accompanying figures focus on an upper arm subset. This upper arm includes both the elbow and wrist, so that the system cares for a hinge joint and a ball-in-socket joint, respectively. Since the body is made up of combinations of those joints, the apparatus and methods described herein can be extended to accommodate other combinations of joints up to and including a full body suit.

Figure 1:
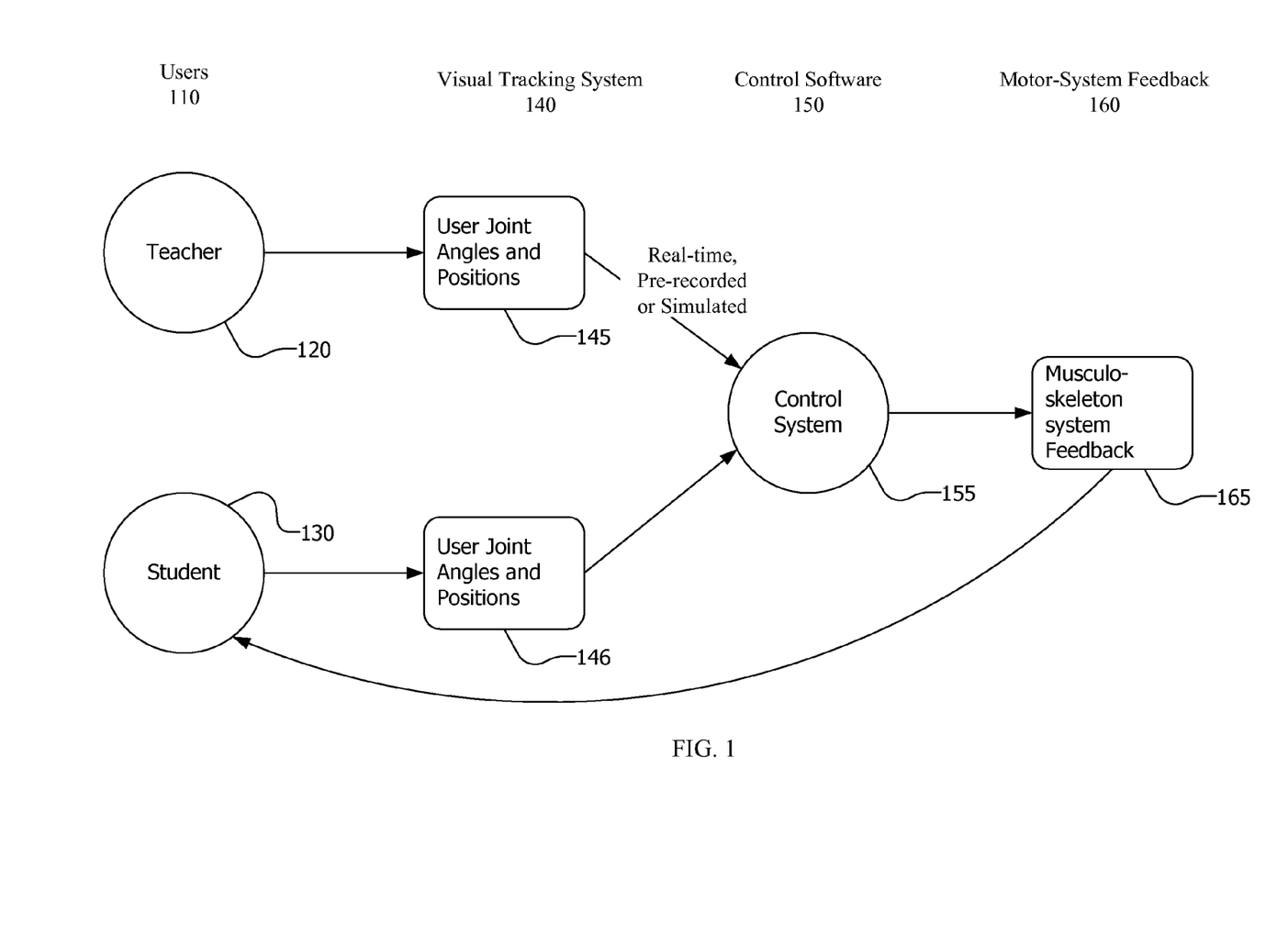
FIG. 1 is a diagram of subsystem interaction.

A diagram of interaction between subsystems is shown in FIG. 1. In this example, two users 110, one a teacher expert 120 and one a student 130, may enter a visual space covered by a visual tracking system 140. The visual tracking system 140 may cover an area of approximately 10'×20' for example, and may achieve 3D positional accuracy of <1.0 mm for over 100 joints tracked at 120 frames/sec. Thus the visual tracking system may be sufficient to model very accurate and rapid human motion. In this example, the feedback from the teacher expert 120 to the student 130 may be synchronous, or near real-time. Alternatively, the motions of the teacher expert 120 may be pre-recorded and stored, or may be simulated.

Control software 150 and control system 155 may send a feedback signal to the student 130 to guide the student 130 towards replicating the motion of the teacher expert 120. The feedback signal may be a function of the error between the motions of the student 120 and the motions of the teacher-expert 120. For example, the feedback signal may be proportional to the error between the motions of the student 120 and the motions of the teacher-expert 120. The feedback gain, or the relationship of the amplitude of the feed back to the magnitude of the error, may be settable by the student 130, or may be set automatically by the control software 150 and control system 155. Initially the feedback may be very weak, as the student's errors would be likely to be too large, but as the student gains more accuracy, the feedback gain may be increased to show more minor errors in motion. The feedback gain may be set automatically based on the student's average errors.

The student's suit may include joint-tracking technology, but may also include an array of output devices or transducers located at all employed joints. More detail on the specific transducer technology is provided below. At time t=0, the student decides to attempt a performance of the new task. As the student 130 moves, the tracking system 140/146 observes the student's behavior, and provides data representative of the student's behavior to the control system 155. The control software 150 and control system 155 compares the data representative of the student's motion to data representative of the teacher's motion or other desired motion. The control system 155 provides tactile control signals to control operation of the transducers incorporated in the student's suit. Using feedback on each muscle, vibrotactile signals are sent directly to the muscles of the student 130, proportionally to the error between the student's joint positions and the teacher's joint positions, to guide the motions of the student towards replicating the motions of the teacher.

The data representative of the desired motion may acquired in real-time by sensing the motions of the teacher. Alternatively, the motions of the teacher may be recorded in advance. Recorded data may be modified or enhanced prior to training the student. Data representative of the desired motion may also be generated from simulated motion. Data from various sources may be combined for use in training.

It has been suggested that to regulate behavior, functions of error should be regulated. Accordingly, at any point during the performance of a maneuver, the student 130 may receive direct tactile/muscular feedback about their inaccuracies in motion. With this direct feedback over initial trials, and guiding the motion and doing so in real-time over some or all joints, mastery of actions may be attained much more rapidly than with visual feedback alone.

Furthermore, this technology, once practiced by a student, may become more immediate—they may be able to learn from muscle stimuli more quickly, and slowly accustom themselves to the point where this system becomes unconscious and forms its own feedback loop with the student's motor system. Artistically, this may extend to the point where multiple students can receive a single signal, and all participate in what may be a completely improvised, yet synchronous, maneuver. More importantly, this could allow a deeply shifted ability to create and retain new muscle memories.

Various methods can influence people's motor systems, while remaining as nonintrusive as possible. Torque application systems and electrical stimulation are options, but inherently bulkier and intrusive to the user. We chose vibrotactile stimulation.

Figure 2:
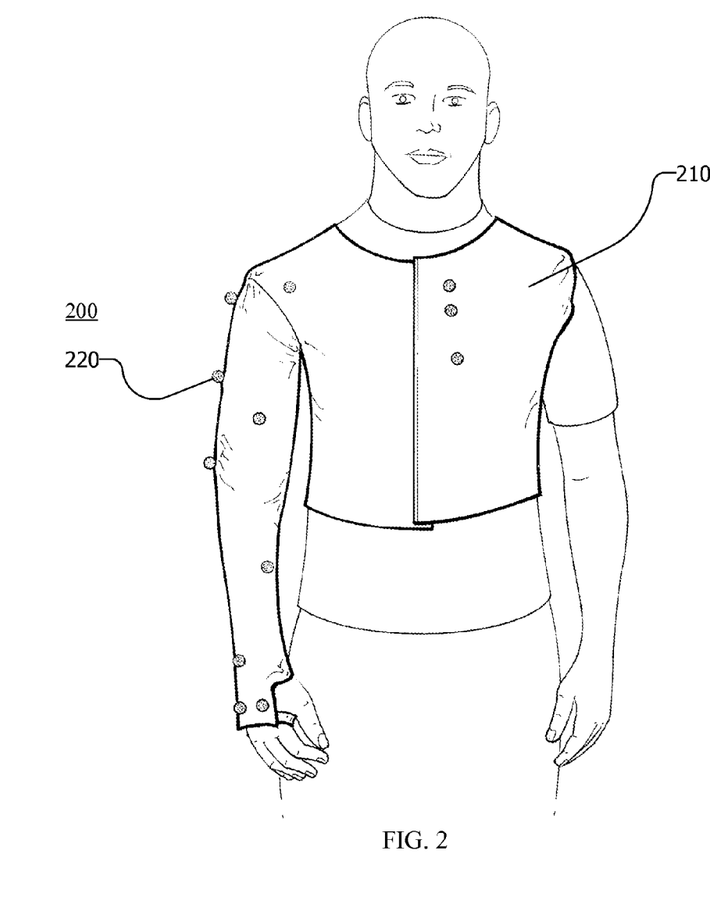
FIG. 2 is a frontal view of user wearing a feedback suit.

With reference to FIG. 2, an example of a tactile feedback apparatus is now described. The example apparatus 200 may be comprised of a custom-made tactile upper body suit 210. The body suit 210 is shown equipped with optical tracking markers 220 (the spherical protrusions) that may be used to track the wearer's movements using an optical tracking system, such as a Vicon tracking system (not shown). The wearer's movements may be tracked by a different optical tracking system, by mechanical transducers such as accelerometers embedded in the body suit 210, or by a combination of optical and mechanical methods. The body suit 210 may incorporate a plurality of vibrotactile transducers (not visible in FIG. 2), such as the Tactaid transducers shown in FIG. 3. Other types of tactile transducers, for example transducers that electrically stimulate the skin, may be incorporated into the body suit 210. The body suit 210 may incorporate eight vibrotactile transducers which, in conjunction with transducer control hardware and firmware (not shown) and compare software (not shown), may regulate five degrees of freedom on the human right arm.

This suit 210 may use transducers on either side of any hinge-type joint (such as the elbow opening/closing) to give a proportional vibrotactile error signal to the joint. For example, on either side of the wrist, a vibrotactile transducer is placed. If the student moves too far in one direction, that direction may vibrate with an amplitude proportional to the angular error. However, the issue of joint rotation cannot be solved in this way. Therefore we use a sequenced vibrotactile response based on human sensory saltation, described below, in order to use the same set of transducers to accomplish both hinge and rotation feedback signals.

The Vicon optical tracking system is a commercial product designed for high-resolution high-bandwidth motion capture. It consists of roughly one dozen near-infrared sensitive cameras with matching strobes, custom hardware and custom software. The teacher-expert or student subject wears a special dark suit with infrared reflectors covering it, in known locations. Each camera tracks the location of bright infrared reflectors, which are triangulated from multiple cameras to form points in 3D space. In order to align those with a specific body, a calibration procedure is performed, after which any movement of the suit on the body will disrupt accuracy of the results.

Figure 3:
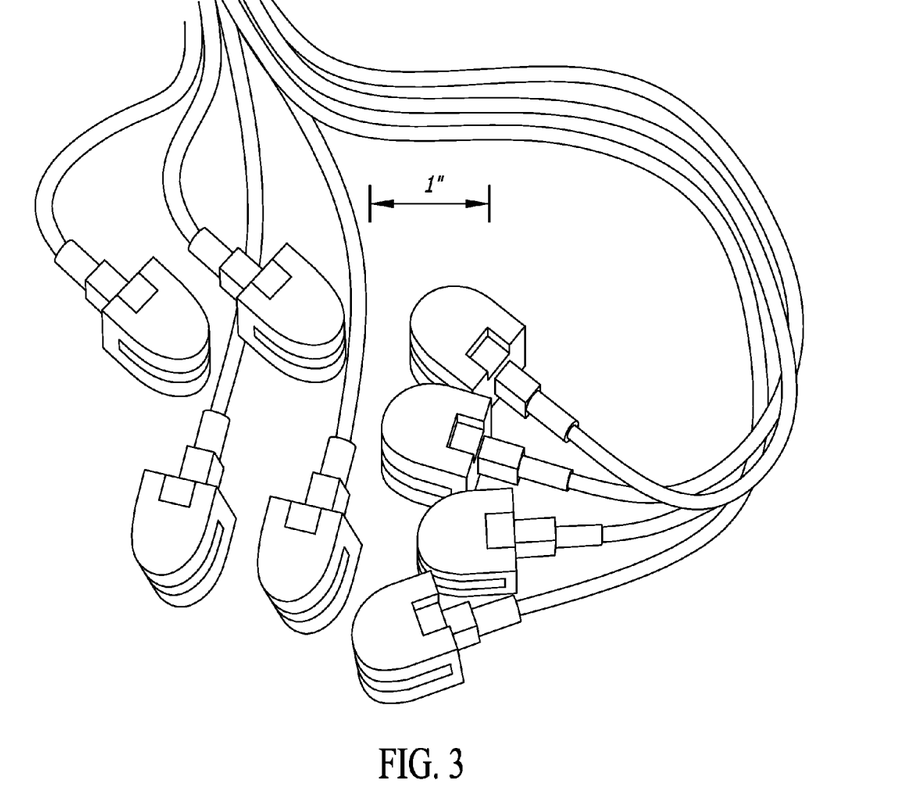
FIG. 3 is a partial view of Tactaid actuators.
Figure 4:
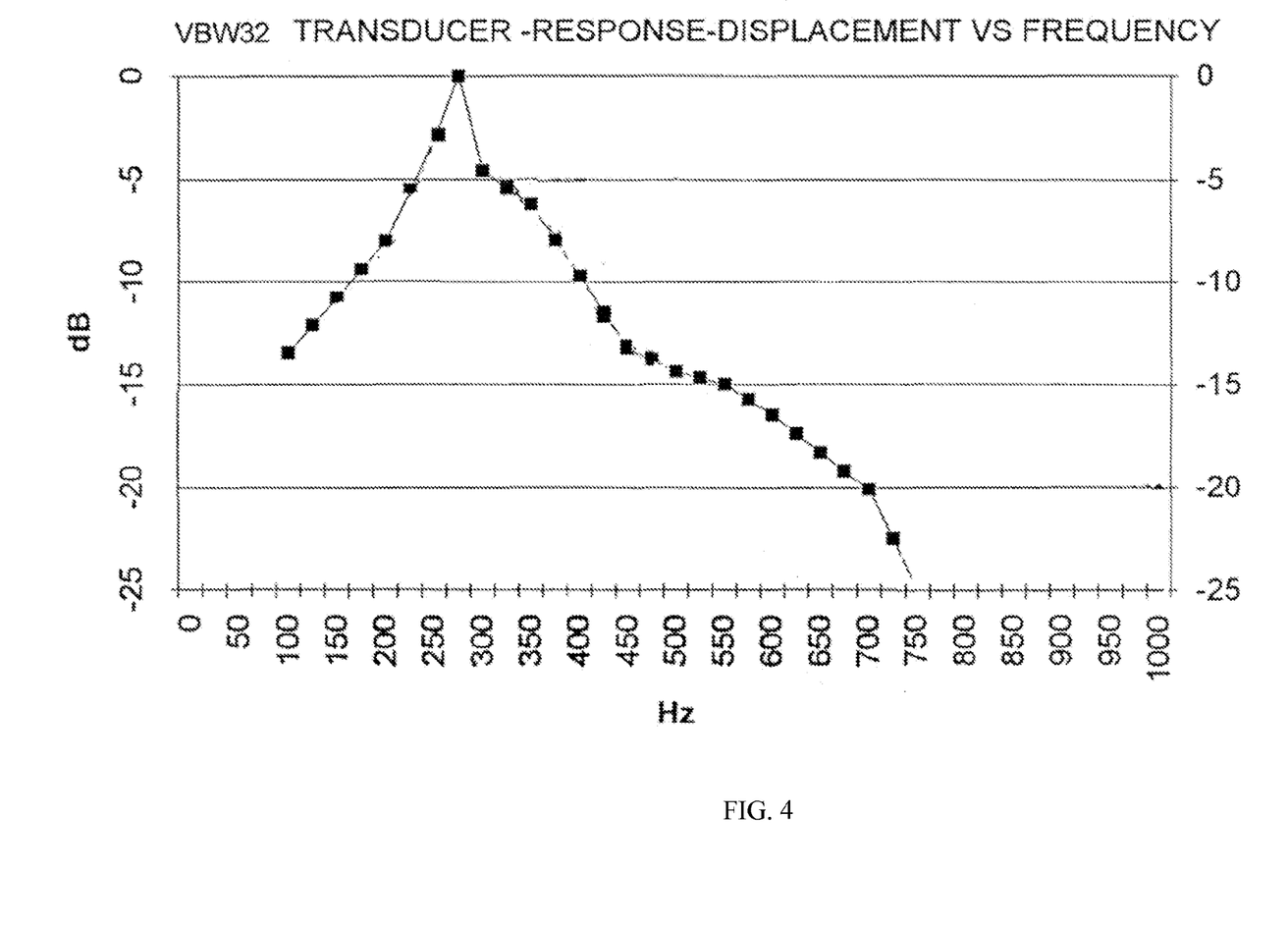
FIG. 4 is a graph of the frequency response of the Tactaid actuator.

The Tactaid actuator, eight of which are shown in FIG. 3, was originally developed for speech-to-tactile translation for the deaf community. This cantilevered resonant actuator provides extremely fast response, fast enough to translate human speech in real time and provide it through a tactile interface, at high enough excursion (linear travel) to be felt on the skin to a reasonable degree. Frequency range of stimulation on the skin reportedly has typically been 230-300 Hz, regarded as optimal for contactors ~7 mm in diameter. These actuators are designed to resonate on the skin at 250 Hz, the peak frequency response of human skin. FIG. 4 shows the frequency response of the Tactaid actuator.

Figure 5:
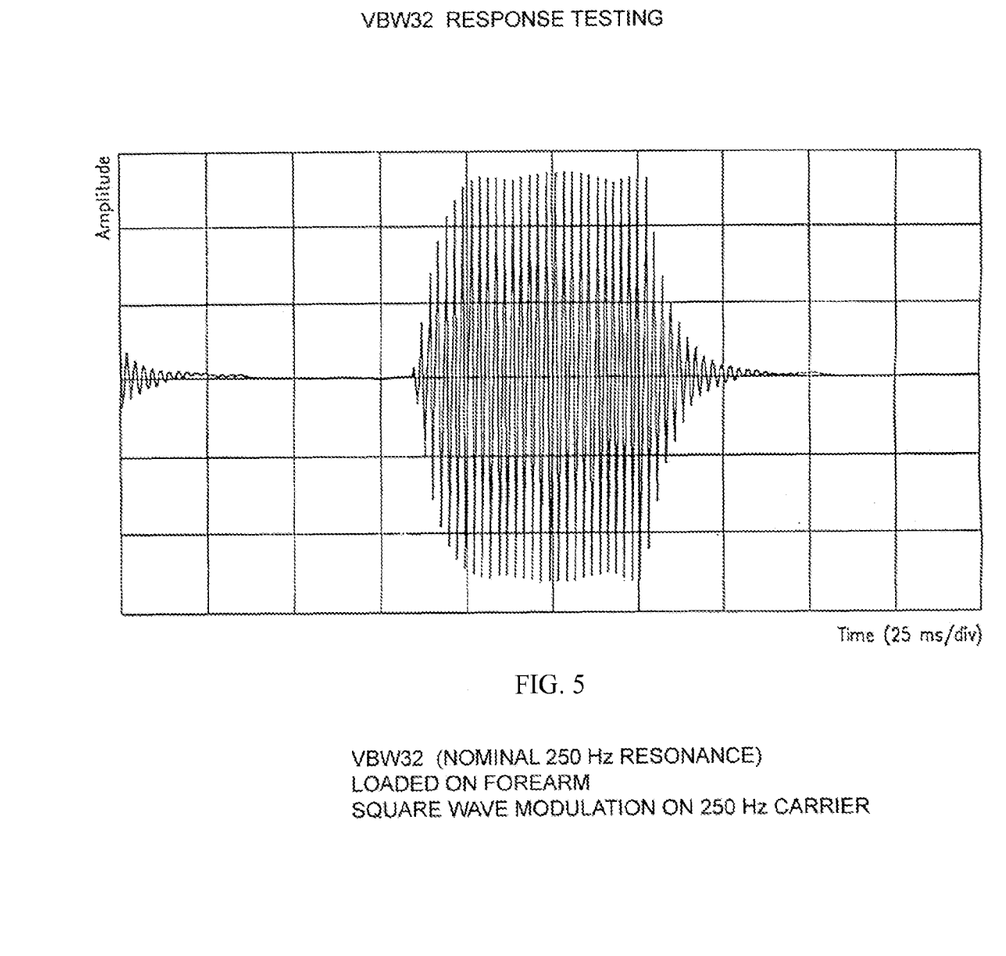
FIG. 5 is a graph of speed of transducer response.

A significant advantage to using a resonant actuator of this design is that it can be turned on and off extremely quickly, thereby enabling very high bandwidth response where needed. A typical vibrating transducer in a cell phone or pager consists of a dc motor with an off-center weight attached to it. As the motor spins around, the weight is thrown back and forth very quickly generating a vibrational pulse. Two problems with this type of transducer are that there is no good way to control vibrational frequency (without sensory feedback) and that the motor needs to spin up from the stopped position in order to reach the correct frequency. Using a resonant actuator, we can completely control the frequency as it always matches our drive frequency, and as shown in FIG. 5, the actuator rings up to full amplitude extremely quickly. We can therefore indicate signals that require high bandwidth, as is the case in many human motor skills. However, other types of transducers may be used if the high bandwidth of a resonant actuator is not required for particular motions.

Figure 6:
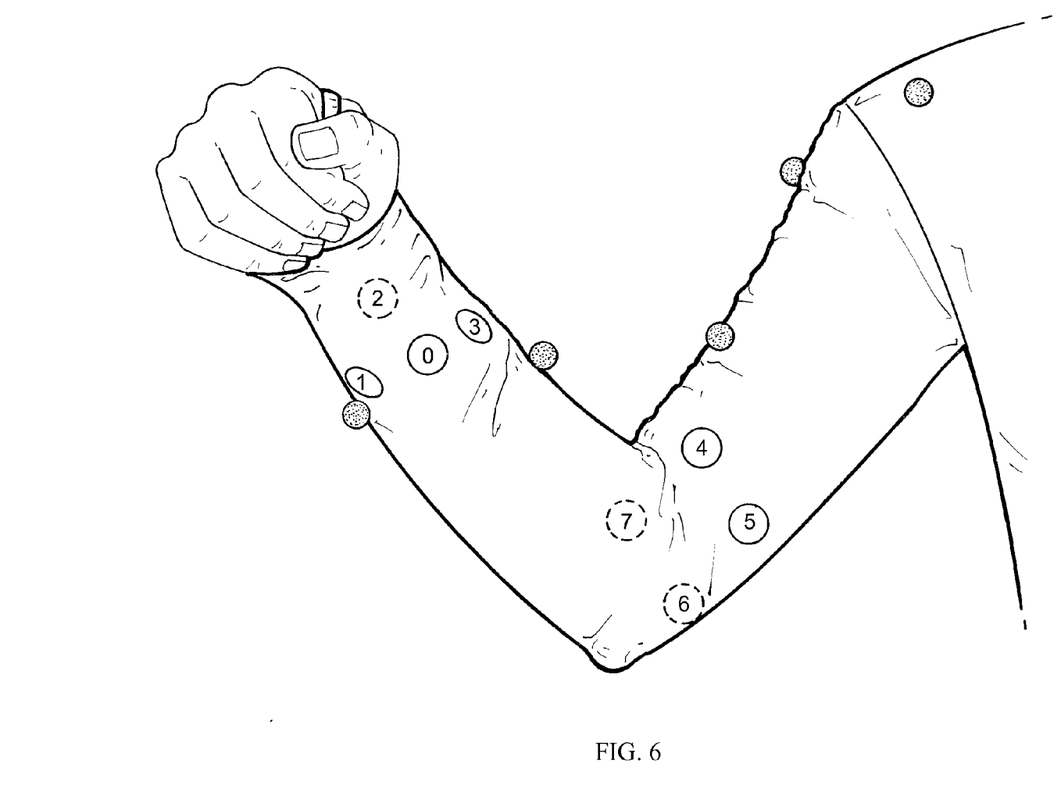
FIG. 6 a partial frontal view of user wearing a feedback suit, showing transducer placement.

Continuing with the example of the upper arm, transducers may be placed at the locations of both the wrist and elbow joints, in a quadrant fashion, along the major and minor axes of rotation of the joints. In this way, we proportionally feedback specific joint angles. Slits cut into the suit allow the transducers to be slid inside, and hook and loop fasteners adhere the outside of the transducer to the inside of the suit. This provides direct transducer-skin contact, to maximize the amount of vibrations felt by the subject. It should be mentioned that no extensive testing was done to find ideal locations of these transducers, so very possibly behavior would be improved with further research into this topic. Although the transducers are disposed within the suit and are not visible in FIG. 6, the locations of the eight transducers used to regulate the five degrees of freedom of the right arm are indicated by circles. A dashed circle indicates the corresponding transducer is placed out of view from this perspective, on the back side of the suit. Each set of four transducers is aligned in a N-W-S-E fashion around the wrist and elbow joints, respectively.

The suit control software is written in JAVA in the IntelliJ environment on a Macintosh G5 computer. It includes several subsystems, used to monitor teacher and student, compare motions, compute signals to be sent to the motor system, and log data for later analysis.

The purpose of the software used in the human experimentation is to monitor the user's motion, while they try to perform a motion shown to them in real-time by a live instructor, or as an image on a video screen. For an image on a video screen, the original motion may have been captured and recorded both as a image and as a set of movements tracked by the Vicon system or other motion capture hardware/software. The recorded set of movements may be compared in real-time to the user's motions, also captured by the Vicon system or other motion capture hardware/software.

The main code loop consists of player updated (teacher), student Vicon capture, error generation, transducer command generation and output, and data logging. The loop occurs as fast as possible, updating video data to keep a normal video play rate, but subsampling Vicon data for higher bandwidth motion response.

Vicon Player Update (Teacher)

All video captures may be stored in a data object consisting of a frame of video data, as well as data defining the joint angles and joint positions of the right arms of the teacher and student. Joint angles are kinematicated in a manner described below. The teacher data structures may contain only the measured joint angles and positions. The student data objects may contain the errors of the student's joints angles and positions, relative to the teacher, as well as the measured parameters.

Student Vicon Capture

As opposed to the teacher motion capture, which may be real-time or prerecorded, the student capture must occur in real-time while giving motor feedback signals. The Vicon system continuously records body positions at approximately 100 Hz. The data shows optical markers 3d position, with a sub-millimeter accuracy. The Vicon system translates the optical marker positions into joint positions through a kinematic model of the users' body, but we are most interested in joint angles. Therefore we use the joint positions to determine the angles by Kinematicating them.

Error Generation

We then compare the angles from the teacher with the angles from the student, and compute an error with a generalized proportional feedback system:

$$\Theta_{error} = K_p(\Theta_{teacher} - \Theta_{student}),$$

where $K_p$ is a constant of proportionality chosen to match the comfort level of the user. A default level of one yields very little error signal (as these angles are in radians), but since some users will by default have higher motion errors or less tolerance for high feedback signal, this is allowed to remain variable.

Note that the signal is chosen to always show error from a reference motion. Experimental evidence shows this to be a promising approach.

It is worth noting that errors in angle are only one of many options for generating error signals. Errors in end effector/joint position, or a hybrid between these two options, may in general lie in higher accord with the true mapping between humans when teaching motion. To be more concrete, when a very tall person and a very short person perform an 'identical' dance routine, it is unknown what function of joint angles or positions is the most salient feature by which to measure accuracy. Most likely it is a dynamically shifting combination of the two, with possible other unknown parameters. Until this is studied, however, joint angles yield a good first approximation. Also, this study will allow more accurate measurements in the future to find those features out.

The one special case that does not represent a linear angular error is the rotational error of the wrist. This may be generated with a saltatory signal. Therefore that signal is sent to the transducer boards in two special channels designated as saltatory signal channels.

Transducer Command Generation and Output

Each transducer channel may be given a sixteen bit integer for PWM duty cycle (strength) and one bit for direction. To generate this, we first clip the signal into the range (−1,1), and then shift this float by a factor of $2^{16}$ and floor it to put it in the range (−65535,65536) as an integer, desired by the transducer control system. We then generate the transducer control packet, which consists of the format:

0xA5 0x28 0x00
$DUTY_0 DUTY_1 DUTY_2 DUTY_3 DUTY_4 DUTY_5 DUTY_6 DUTY_7 SALT_1 SALT_2$
0x00 0x00 0x00 0x00 0x00 0x00 0x00 0x00 0x00 0x00 0x00 0x00 CHECKSUM, where the variables indicate the following parameters:

| Name | Description |
| --- | --- |
| DUTY0 | Wrist Front Transducer |
| DUTY1 | Wrist Left Transducer |
| DUTY2 | Wrist Back Transducer |
| DUTY3 | Wrist Right Transducer |
| DUTY4 | Elbow Front Transducer |
| DUTY5 | Elbow Left Transducer |
| DUTY6 | Elbow Back Transducer |
| DUTY7 | Elbow Right Transducer |
| SALT1 | Wrist Saltation Forward Signal |
| SALT2 | Wrist Saltation Backward Signal |

The 0xA5 initiates the signal to the transducer control boards, and 0x28 signifies that we are sending desired positions/duty cycles for the transducers. The checksum at the end rids us of communication errors.

Note that since all transducers and saltatory signals work as opponent processes, the opponent transducers should never both be on at the same time, except in the case of superposition of a linear error and a saltatory signal.

Data Logging

Every aspect of information measurable during this process may be logged into a user study file, for future reference or data analysis. The user study file may be labeled by date and may or may not contain a personal reference to the participant.

In this manner, each video set can be repeated as often as possible, and any number of videos can be shown, while still stored in this simple data format. The master parameters store what type of feedback the user is receiving, and every frame stores all of the relevant info about joint positions and angles. All of the data may be stored in a JSX object format, serialized so that we can later open this object and format it for data analysis. Also, the JSX format allows a human-readable serialized output so that if for some reason, the serialization breaks down, we can still view the file and extract the relevant data. Given the amount of data stored in this experiment every frame, the data log files are many megs and the overall data structures are several gigabytes worth of raw information.

Control Hardware

A transducer control hardware system may be used that allows one computer to control many independent degrees of freedom (transducers), with the transducer control hardware handling all of the low level commands and feedback systems.

The transducer control hardware system used for the apparatus described herein is a modular, 8-channel, dc motor control system, allowing independent feedback control of up to approximately 60 Volt motors, with peak currents of roughly 2A each. It is comprised of the following subsystems: voltage regulation, an AVR microcontroller, a serial computer interface, a feedback control system, and an FPGA coprocessor.

Each vibratory signal is generated as the product of a high frequency (roughly 40 kHz) pulse width modulated signal to give duty cycle and a 250 Hz square wave, to generate the vibration in the resonant response frequency of the skin. The duty cycle determined by the software is sent to the microcontroller which generates the 250 Hz square pulsed signal. The 250 Hz square pulsed signal is sent to the FPGA, which then generates signals to drive the motor controllers, each of which includes four MOSFET devices in a conventional H-bridge configuration.

Motor Control Board Software

The software running on the AVR microcontroller on the motor control board is written in C and programmed onto the AVR with an AVR-ISP.

Upon startup, the AVR sets up a 16-bit internal timer interrupt script. The oscillator runs at 11.059 Mhz, an ideal rate for serial communication (low percentage error), so by executing an interrupt every 11059 clock cycles, and using this interrupt to trigger our main loop, we are insured to have our main loop occur at a 1 kHz frequency. Since we desire a perfect 250 Hz output signal, as this is the resonant frequency of the skin, an even multiple of this makes the rest of our coding much easier. The AVR also sets up 57.6 kbps serial communication, to receive host computer signal commands.

Several things happen during the 1 kHz control loop. First, we always check to see whether we have received any new host commands from the driving computer. These commands instruct not only the duty cycle of the output transducers, but also send the saltation amounts in channels 9 and 10 to be computed by the AVR and added to the original duty cycles. We do this because the saltation signals must move from transducer to transducer more quickly than the host computer and hardware communicate. It would therefore be impossible to control saltation accurately without a roughly 100 Hz communication rate, which we cannot guarantee.

Since we desire a 250 Hz square wave output, we downsample the 1 kHz by a factor of 2 to generate a 500 Hz signal. Every $\frac{1}{500}$ sec, we switch direction of our output signal, which creates a 250 Hz output.

We then subsample another clock down to roughly 35 Hz for our saltation signal. This controls how often the saltatory signal jumps to the neighboring transducer. Since we use four transducers for our saltation, this yields a roughly 9 Hz saltatory rotation around the wrist. The direction of saltation is sent through channels 9 and 10, so every time this subsampled clock recycles to 0, we either increment or decrement the desired chosen wrist transducer, to carry it circularly around the wrist. There is a subsampled clock that counts half of each saltation cycle (15 of 30 cycles) and determines whether or not to turn the pulse on or off. This duty cycle influences the feel of the saltatory pulses, with a shorter on pulse yielding a more 'tap' type feeling.

Finally, the loop applies the commanded errors to each channel, and superimposes the saltatory signal on top of the original error signal. If the superimposed signal goes out of range, we clip it to its maximum value (−65535,65536). Then, this duty cycle value and direction signal are sent to the FPGA for low level PWM generation. The FPGA receives this duty cycle, and then generates a roughly 40 kHz PWM signal which is then amplified to motor level by the H-bridge circuit described above.

In sum, this disclosure shows how to maximize the efficiency for motor skill learning or relearning in a variety of tasks, through direct muscle learning from a tactile robotic biofeedback system, as well as to remove the need for constant expert presence during the learning process. In essence, to make learning automatic and natural for anybody, to make people feel real-time feedback from an expert, from the first time they attempt a new skill. To remove the need for an inadequate spoken language to try to teach what is otherwise so fundamental to our bodies, through the feedback of a robotic suit. Experimental results indicate that a non-torque based vibrotactile feedback accelerates the learning of motor skills. If this approach is also effective for rehabilitation, it could represent a large shift in the way we heal patients. Compared to torque feedback, vibrotactile feedback is less bulky, less intrusive to one's behavior, can be worn unnoticeably, and requires the user to fully power the desired motion, to further train their motor system from first performance.

This work has many potential applications. Neurological trauma and training of persons with disabilities is the most immediate. Static posture analysis and retraining for those with repetitive strain injuries is a possible area for development as well. Finally, the use in the sports and arts industries is varied, from swinging a golf club, to playing guitar, to the use of a tactile signal itself as an artist medium for communication between artists.

Student tactile-suits could become a standard for accelerated learning in dance, sports, rehabilitation, musical instruments, sign language acquisition—in short, it could change the way we learn how to move.

Closing Comments

The foregoing is merely illustrative and not limiting, having been presented by way of example only. Although examples have been shown and described, it will be apparent to those having ordinary skill in the art that changes, modifications, and/or alterations may be made.

Although many of the examples presented herein involve specific combinations of method acts or system elements, it should be understood that those acts and those elements may be combined in other ways to accomplish the same objectives. With regard to flowcharts, additional and fewer steps may be taken, and the steps as shown may be combined or further refined to achieve the methods described herein. Acts, elements and features discussed only in connection with one embodiment are not intended to be excluded from a similar role in other embodiments.

For means-plus-function limitations recited in the claims, the means are not intended to be limited to the means disclosed herein for performing the recited function, but are intended to cover in scope any means, known now or later developed, for performing the recited function.

As used herein, "plurality" means two or more.

As used herein, a "set" of items may include one or more of such items.

As used herein, whether in the written description or the claims, the terms "comprising", "including", "carrying", "having", "containing", "involving", and the like are to be understood to be open-ended, i.e., to mean including but not limited to. Only the transitional phrases "consisting of" and "consisting essentially of", respectively, are closed or semi-closed transitional phrases with respect to claims.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, "and/or" means that the listed items are alternatives, but the alternatives also include any combination of the listed items.

It is claimed:

1. A process for motor learning, for teaching motion, or for rehabilitation of a student, the student having a motor sensory system, the process comprising
   coupling one or more transducers to the student around at least one joint, the transducers for providing kinesthetic sensations to the student through its motor sensory system
   sensing the motion of the at least one joint
   comparing the sensed motion to a desired motion
   deriving tactile control signals from a difference between the sensed motion and the desired motion
   using the tactile control signals to control operation of the transducers to guide the student to replicate the desired motion.

2. The process of claim 1, wherein
   the desired motion comprises a recorded or simulated teaching motion played at a speed or learning rate selected by the student or selected specifically for the student.

3. The process of claim 1, wherein
   the student is an animal selected from the group comprising a mammal, a bird, a fish, a reptile and an amphibian.

4. The process of claim 1, wherein
   the transducers are vibrotactile stimulators and the kinesthetic sensations comprise vibrotactile stimulation.

5. The process of claim 1, wherein
   the desired motion comprises real-time feedback from a teacher to the student.

6. The process of claim 5, further comprising
   sensing a motion of the teacher at a joint of the teacher corresponding to the at least one joint of the student
   providing a kinesthetic sensation at the at least one joint of the student, the kinesthetic sensation to guide the student to replicate the motion of the teacher's joint.

7. The process of claim 6, wherein
   the kinesthetic sensation is a function of the error between the motion of the teacher at the joint and the motion of the student at the joint.

8. The process of claim 6, further comprising
   providing a human sensory saltation at the at least one joint of the student.

9. The process of claim 6, further comprising
sensing a series of motions of the teacher
providing a corresponding series of kinesthetic sensations to the student.

10. A non-transitory storage medium storing instructions that, when executed by a computing device, cause the computing device to perform operations comprising
receiving data representative of a motion of at least one joint of a student
comparing the received data to data representative of a desired motion
deriving tactile control signals based on a difference between the data representative of a motion of at least one joint of the student and the data representative of a desired motion
providing tactile control signals to control the operation of plural vibrotactile devices disposed on a garment worn by the student to guide motions of the student to replicate the desired motion.

11. The storage medium of claim 10, wherein the data representative of a desired motion may be selected from the group considering of real time data from sensing the motion of a teacher, recorded data from sensing the motion of a teacher, modified recorded data, data from simulated motion, and combinations thereof.

12. A method for teaching a motor skill to a student, comprising:
sensing a movement of the student performing the motor skill,
comparing the movement of the student to a prerecorded movement of an expert performing the motor skill,
providing tactile feedback to the student to guide the student to replicate the movement of the expert by providing control signals to one or more tactile transducers embedded in a garment worn by the student, the control signals derived from a difference between the sensed movement of the student and the prerecorded movement of the expert.

13. The method of teaching a motor skill to a student of claim 12, wherein comparing the movement of the student to the prerecorded movement of an expert further comprises comparing sensed joint positions and angles of the student with prerecorded data representative of the joint positions and angles of the expert while performing the motor skill.

14. The method of teaching a motor skill to a student of claim 12, wherein the motor skill is a sports skill, and the expert is a professional athlete.

15. The method of teaching a motor skill to a student of claim 14, wherein the motor skill is a golf swing, and the expert is a professional golfer.

16. The method of teaching a motor skill to a student of claim 12, wherein the motor skill is the playing of a musical instrument, and the expert is a professional musician or music instructor.

17. The method of teaching a motor skill to a student of claim 12, wherein the motor skill is a dance movement, and the expert is a professional dancer or dance instructor.

18. The method of teaching a motor skill to a student of claim 12, wherein the motor skill is the operation of a vehicle or other equipment, and the expert is an instructor.

* * * * *